(12) United States Patent
Mizuno et al.

(10) Patent No.: US 8,168,796 B2
(45) Date of Patent: May 1, 2012

(54) FLUORESCENT AGENT HAVING ETHYNYL GROUP

(75) Inventors: Kazuhiko Mizuno, Osaka (JP);
Hideyuki Takagaki, Wakayama (JP);
Hirokazu Iwahashi, Wakayama (JP);
Kaname Inoue, Wakayama (JP)

(73) Assignee: Nippon Chemical Works Co., Ltd., Wakayama (JP)

( * ) Notice: Subject to any disclaimer, the term of this patent is extended or adjusted under 35 U.S.C. 154(b) by 0 days.

(21) Appl. No.: 12/864,313

(22) PCT Filed: Jan. 19, 2009

(86) PCT No.: PCT/JP2009/050631
§ 371 (c)(1),
(2), (4) Date: Jul. 23, 2010

(87) PCT Pub. No.: WO2009/093537
PCT Pub. Date: Jul. 30, 2009

(65) Prior Publication Data
US 2010/0298573 A1 Nov. 25, 2010

(30) Foreign Application Priority Data
Jan. 25, 2008 (JP) .................................. 2008-014591

(51) Int. Cl.
*C07D 231/06* (2006.01)
*C07D 311/82* (2006.01)
(52) U.S. Cl. .................. 548/110; 548/365.1; 548/364.4; 549/241; 549/280
(58) Field of Classification Search .................. 548/110, 548/356.1, 364.4; 549/214, 280
See application file for complete search history.

(56) References Cited

U.S. PATENT DOCUMENTS
2008/0265750 A1   10/2008   Matsumoto et al.

FOREIGN PATENT DOCUMENTS
| JP | 2002-69013 | 3/2002 |
| JP | 2006-104124 | 4/2006 |
| JP | 2006-117593 | 5/2006 |
| WO | 01/68635 | 9/2001 |

OTHER PUBLICATIONS

Wu, Jie. Synthesis of 4-Substituted Coumarins via the Palladium-Catalyzed Cross-Couplings of 4-Tosylcoumarins with Terminal Acetylenes and Organozinc Reagents. J. Org. Chem. (66), (2001), 3642-3645.*
Form PCT/IB/338 together with translation of International Preliminary Report on Patentability dated Sep. 16, 2010 in International (PCT) Application No. PCT/JP2009/050631.
International Search Report issued Apr. 21, 2009 in International (PCT) Application No. PCT/JP2009/050631.
Otto Neunhoeffer et al., "Synthesis and fluorescence of substituted 2-pyrazolines", Chemische Berichte, vol. 86, pp. 226-231, 1953.
John E.T. Corrie et al., "Synthesis and fluorescence properties of substituted 7-aminocoumarin-3-carboxylate derivatives", Journal of Heterocyclic Chemistry, 37(6), pp. 1447-1455, 2000.
K.U. Joseph et al., "Search for fluorescent brighteners. I. Synthesis of 2-(3'-coumarinyl)benzoxazoles and their fluorescence", Journal of the Indian Chemical Society, 56(5), pp. 505-507, 1979.
Arvind P. Borse et al., "A new synthesis of 3-chlorocoumarins and synthesis of isocoumestan", Indian Journal of Chemistry, Section B: Organic Chemistry Including Medicinal Chemistry, 26B(12), pp. 1180-1181, 1987.

* cited by examiner

*Primary Examiner* — Rebecca Anderson
*Assistant Examiner* — Samantha Shterengarts
(74) *Attorney, Agent, or Firm* — Wenderoth, Lind & Ponack, L.L.P.

(57) ABSTRACT

There are provided novel fluorescent agents, such as pyrazoline compounds represented by formula (I):

[Chemical Formula 1]

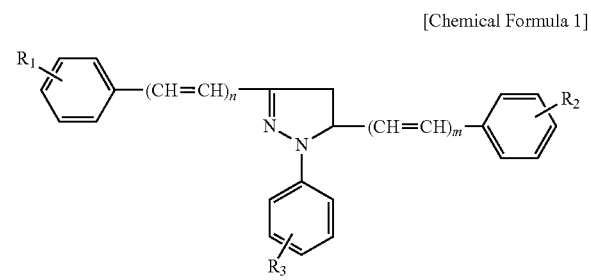

(wherein $R_1$, $R_2$ and $R_3$ are as defined in the specification), having an ethynyl group in the molecule,
which have high absorptivity in the ultraviolet-visible short wavelength range (for example, 350 nm-420 nm).

2 Claims, No Drawings

FLUORESCENT AGENT HAVING ETHYNYL GROUP

TECHNICAL FIELD

The present invention relates to a novel fluorescent agent comprising an ethynyl group in the molecule, which has high absorptivity in the ultraviolet-visible short wavelength range.

BACKGROUND ART

Fluorescent agents are used for various uses, among which the following are typical. In photosensitive resin-related fields, additives used as constituent materials include penetrant additives for the purpose of increasing visibility in nondestructive inspection methods such as their representative penetrant flaw inspection methods, and additives for optical inspection (AOI) in photoresist-related fields that have increasingly become automated with higher speeds in recent years. They are also used as photosensitizers for dry films used for patterning of circuit boards. Other uses include as additives for ultraviolet absorption films that cut harmful ultraviolet rays from sunlight and ultraviolet rays generated from illumination devices such as fluorescent lamps that attract flying insects, and as additives for ultraviolet absorption films that cut ultraviolet rays from sunlight and fluorescent lamps to prevent discoloration of photographs and liquid crystal displays.

On the other hand, compounds with certain types of coumarin backbones are known as fluorescent agents with ethynyl groups in the molecule. Specifically, substituted and unsubstituted 3-phenylethynylcoumarins are disclosed as organic coloring agents in Patent document 1. Although their purposes of use differ, Patent document 2 mentions that aromatic compounds containing acetylene groups (ethynyl groups) can be used for vapor deposition polymerization. Vapor deposition polymerized monomers are used as vapor deposition polymerization thin-films in electronic light emitting elements. The aromatic ring backbones may be compounds with various and diverse backbones, and coumarin is disclosed as one of them.

[Patent document 1] WO01/68635A2
[Patent document 2] Japanese Unexamined Patent Application Publication No. 2002-69013

SUMMARY OF INVENTION

Technical Problem

When conductor pattern examination is carried out by Automatic Optical Inspection (AOI) of printed wiring boards in photosensitive resin-related fields, the scattering of light is increased when a large amount of fluorescent agent is used to increase sensitivity of the detector used for detection of fluorescence reflection from the resin layers other than the conductor (an insulating layer and fluorescent-containing layer), and this prevents accurate pattern examination and precludes application to high-speed AOI.

Furthermore, ultraviolet curing photosensitive resists are cured by irradiation of ultraviolet rays, and increasing the amount of fluorescent agent used to reduce the exposure dose results in a drawback in that the curing of the surface occurs before curing of the deep sections of the resin.

For use as an ultraviolet absorption film to cut ultraviolet rays, increasing the amount of fluorescent agent used to cut more ultraviolet rays especially at the long wavelength end, when using a known fluorescent agent, results in the drawback of yellow colorlation of the film and reduced transparency.

Fluorescent agents with higher ultraviolet absorptivity (molecular absorption coefficients) are therefore necessary to counter these problems.

Solution to Problem

The present invention provides compounds represented by the following formula (I), (III) or (XI) that are suitable as fluorescent agents with high absorptivity in the ultraviolet-visible short wavelength range, as fluorescent agents that overcome the problems mentioned above.

Specifically, according to one mode of the invention there is provided a pyrazoline compound represented by formula (I):

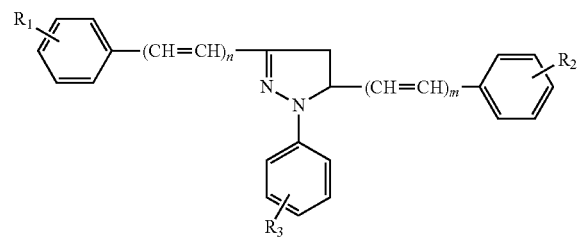

[Chemical Formula 1]

[wherein $R_1$, $R_2$ and $R_3$ each independently represents hydrogen, halogen, $C_{1-8}$ alkyl, $C_{1-8}$ alkoxy, amino, an alkylamino or dialkylamino group having a $C_{1-8}$ alkyl group, sulfomethyl, sulfoamide, or a trimethylsilylethynyl group or a substituted or unsubstituted phenylethynyl group represented by formula (II):

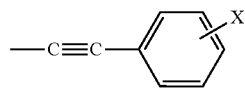

[Chemical Formula 2]

(wherein X represents hydrogen, halogen, $C_{1-3}$ alkyl or $C_{1-3}$ alkoxy),
with the proviso that at least one of $R_1$, $R_2$ and $R_3$ represents a trimethylsilylethynyl group or phenylethynyl group; and m and n each represent 0 or 1].

According to another mode of the invention there is provided a coumarin compound represented by formula (III):

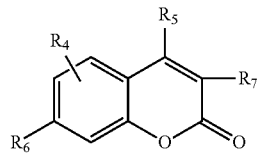

[Chemical Formula 3]

[wherein $R_4$ represents hydrogen, $C_{1-4}$ alkyl, $C_{1-4}$ alkoxy, halogen, or
a trimethylsilylethynyl group or a substituted or unsubstituted phenylethynyl group represented by formula (X):

[Chemical Formula 4]

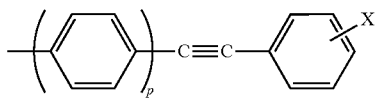

(wherein X represents hydrogen, halogen, $C_{1-3}$ alkyl or $C_{1-3}$ alkoxy; and
p represents an integer of 0-2);

$R_5$ represents hydrogen, $C_{1-4}$ alkyl, cyano, $CF_3$, phenyl or a trimethylsilylethynyl group or a substituted or unsubstituted phenylethynyl group represented by formula (X):

[Chemical Formula 5]

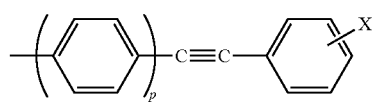

(wherein X represents hydrogen, halogen, $C_{1-3}$ alkyl or $C_{1-3}$ alkoxy; and
p represents an integer of 0-2);

$R_6$ represents hydrogen, $C_{1-4}$ alkyl, $C_{1-4}$ alkoxy, amino or an alkylamino or dialkylamino group having a $C_{1-4}$ alkyl, or NH-acyl, or a triazole group represented by formula (IV):

[Chemical Formula 6]

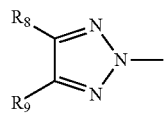

(wherein $R_8$ and $R_9$ each independently represents hydrogen, $C_{1-3}$ alkyl, $C_{1-3}$ alkoxy or a substituted or unsubstituted phenyl group),
a benzotriazole group represented by formula (V):

[Chemical Formula 7]

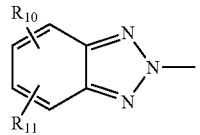

(wherein $R_{10}$ and $R_{11}$ each independently represents $C_{1-3}$ alkyl or $C_{1-3}$ alkoxy),
a naphthotriazole group represented by formula (VI):

[Chemical Formula 8]

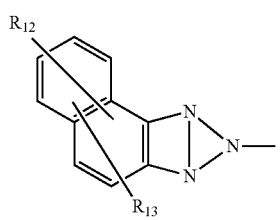

(wherein $R_{12}$ and $R_{13}$ each independently represents hydrogen, $C_{1-4}$ alkyl, $C_{1-4}$ alkoxy or halogen), a pyrazoline group represented by formula (VII):

[Chemical Formula 9]

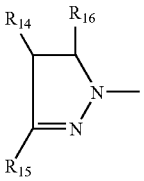

(wherein $R_{14}$, $R_{15}$ and $R_{16}$ each independently represents hydrogen, $C_{1-4}$ alkyl or a substituted or unsubstituted phenyl group), or
a trimethylsilylethynyl group, or a substituted or unsubstituted phenylethynyl group represented by formula (X):

[Chemical Formula 10]

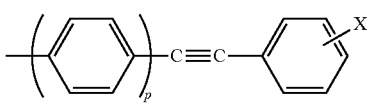

(wherein X represents hydrogen, halogen or $C_{1-3}$ alkyl or $C_{1-3}$ alkoxy; and
p represents an integer of 0-2);

$R_7$ represents hydrogen, cyano, acetyl, carboxyl or phenyl represented by formula (VIII):

[Chemical Formula 11]

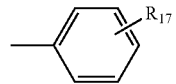

(wherein $R_{17}$ represents hydrogen, $C_{1-3}$ alkyl or halogen),
a heterocyclic group represented by formula (IX):

[Chemical Formula 12]

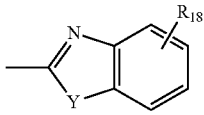

(wherein Y represents O, S, NH, N—$CH_3$ or N—$C_2H_5$; and $R_{18}$ represents hydrogen, $C_{1-3}$ alkyl, $C_{1-3}$ alkoxy or halogen), or
a trimethylsilylethynyl group, or a substituted or unsubstituted phenylethynyl group represented by formula (X):

[Chemical Formula 13]

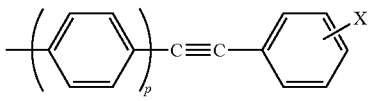

(wherein X represents hydrogen, halogen, or $C_{1-3}$ alkyl or $C_{1-3}$ alkoxy; and
p represents an integer of 0-2), with the proviso that at least one of $R_4$, $R_5$, $R_6$ and $R_7$ represents a trimethylsilylethynyl group or phenylethynyl group, and when $R_7$ represents a phenylethynyl group, $R_6$ represents a group other than hydrogen].

According to another mode of the invention there is provided a coumarin compound represented by formula (XI):

[Chemical Formula 14]

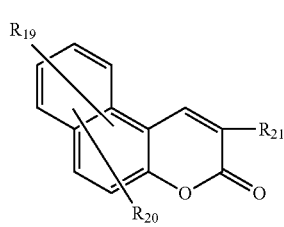

[wherein $R_{19}$ and $R_{20}$ each independently represents hydrogen, $C_{1-4}$ alkyl, $C_{1-4}$ alkoxy or halogen; and $R_{21}$ represents trimethylsilylethynyl or a substituted or unsubstituted phenylethynyl group represented by formula (XII):

[Chemical Formula 15]

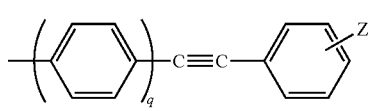

(wherein Z represents halogen, $C_{1-3}$ alkyl or $C_{1-3}$ alkoxy; and q represents an integer of 0-2)].

Advantageous Effects of Invention

As will become apparent by the description in the examples, comparative examples and reference examples, the pyrazoline compounds and coumarin compounds of the invention are compounds with high absorptivity (molecular absorption coefficients) in the ultraviolet-visible short wavelength range, and can be used as fluorescent agents for a variety of uses.

DESCRIPTION OF EMBODIMENTS

The following may be mentioned as representative examples of pyrazoline compounds and coumarin compounds of the invention.
1-Phenyl-3-(4-trimethylsilylethynylphenyl)-5-phenylpyrazoline
1-Phenyl-3-(4-trimethylsilylethynylphenyl)-5-(4-tert-butylphenyl)pyrazoline
1-Phenyl-3-(4-trimethylsilylethynylphenyl)-5-(4-iso-propylphenyl)pyrazoline
1-Phenyl-3-(4-trimethylsilylethynylphenyl)-5-(4-tert-octylphenyl)pyrazoline
1-Phenyl-3-(4-trimethylsilylethynylphenyl)-5-(3-chlorophenyl)pyrazoline
1-Phenyl-3-(4-trimethylsilylethynylphenyl)-5-(4-methoxyphenyl)pyrazoline
1-Phenyl-3-(4-trimethylsilylethynylphenyl)-5-(3-methoxyphenyl)pyrazoline
1-Phenyl-3-(4-trimethylsilylethynylphenyl)-5-(4-diethylaminophenyl)pyrazoline
1-Phenyl-3-(3-trimethylsilylethynylphenyl)-5-(4-tert-butylphenyl)pyrazoline
1-(4-Methylphenyl)-3-(4-trimethylsilylethynylphenyl)-5-phenylpyrazoline
1-(4-Chlorophenyl)-3-(4-trimethylsilylethynylphenyl)-5-(4-tert-butylphenyl)pyrazoline
1-Phenyl-3-(4-trimethylsilylethynylphenyl)-5-(4-trimethylsilylethynylphenyl)pyrazoline
1-Phenyl-3-(4-phenylethynylphenyl)-5-phenylpyrazoline
1-Phenyl-3-(4-phenylethynylphenyl)-5-(4-tert-butylphenyl)pyrazoline
1-Phenyl-3-(4-phenylethynylphenyl)-5-(4-iso-propylphenyl)pyrazoline
1-Phenyl-3-(4-phenylethynylphenyl)-5-(4-tert-octylphenyl)pyrazoline
1-Phenyl-3-(4-phenylethynylphenyl)-5-(3-chlorophenyl)pyrazoline
1-Phenyl-3-(4-phenylethynylphenyl)-5-(4-methoxyphenyl)pyrazoline
1-Phenyl-3-(4-phenylethynylphenyl)-methoxyphenyl)pyrazoline
1-Phenyl-3-(4-phenylethynylphenyl)-5-(4-diethylaminophenyl)pyrazoline
1-Phenyl-3-(4-phenylethynylphenyl)-5-styrylpyrazoline
1-Phenyl-3-(4-phenylethynylphenyl)-5-(4-tert-butylstyryl)pyrazoline
1-Phenyl-3-(4-phenylethynylphenyl)-5-(4-methoxystyryl)pyrazoline
1-Phenyl-3-(4-phenylethynylphenyl)-5-(3-chlorostyryl)pyrazoline
1-Phenyl-3-(4-phenylethynylphenyl)-5-(4-diethylaminostyryl)pyrazoline
1-Phenyl-3-(4-phenylethynylphenyl)-5-phenylpyrazoline
1-Phenyl-3-(4-phenylethynylphenyl)-5-(4-tert-butylphenyl)pyrazoline
1-(4-Methylphenyl)-3-(4-phenylethynylphenyl)-5-phenylpyrazoline
1-(4-Chlorophenyl)-3-(4-phenylethynylphenyl)-5-(4-tert-butylphenyl)pyrazoline
1-Phenyl-3-(4-phenylethynylphenyl)-5-(4-phenylethynyl)pyrazoline
1-Phenyl-3-(3-phenylethynylphenyl)-5-(4-tert-butylphenyl)pyrazoline
1-Phenyl-3-[4-(p-chlorophenylethynyl)phenyl]-5-phenylpyrazoline
1-Phenyl-3-[4-(p-chlorophenylethynyl)phenyl]-5-(4-tert-butylphenyl)pyrazoline
1-Phenyl-3-[4-(p-chlorophenylethynyl)phenyl]-5-(4-iso-propylphenyl)pyrazoline
1-Phenyl-3-[4-(p-chlorophenylethynyl)phenyl]-5-(4-tert-octylphenyl)pyrazoline
1-Phenyl-3-[4-(p-chlorophenylethynyl)phenyl]-5-(3-chlorophenyl)pyrazoline
1-Phenyl-3-[4-(p-chlorophenylethynyl)phenyl]-5-(4-methoxyphenyl)pyrazoline
1-Phenyl-3-[4-(p-chlorophenylethynyl)phenyl]-5-(3-methoxyphenyl)pyrazoline
1-Phenyl-3-[4-(p-chlorophenylethynyl)phenyl]-5-(4-diethylaminophenyl)pyrazoline
1-(4-Nitrophenyl)-3-[4-(p-chlorophenylethynyl)phenyl]-5-phenylpyrazoline
1-Phenyl-3-(4-trimethylsilylstyryl)-5-(4-trimethylsilylstyryl)pyrazoline
1-Phenyl-3-(4-phenylethynylstyryl)-5-(4-phenylethynylstyryl)pyrazoline
1-Phenyl-3-(3-trimethylsilylstyryl)-5-(4-trimethylsilylstyryl)pyrazoline 1-Phenyl-3-(3-phenylethynylstyryl)-5-(3-phenylethynyl-styryl)pyrazoline
1-Phenyl-3-(2-trimethylsilylstyryl)-5-(4-trimethylsilyl-styryl)pyrazoline
1-Phenyl-3-(2-phenylethynylstyryl)-5-(2-phenylethynyl-styryl)pyrazoline
7-Dimethylamino-3-trimethylsilylethynyl-4-methylcoumarin
7-Dimethylamino-3-[4-(trimethylsilylethynyl)phenyl]coumarin
7-Dimethylamino-3-[4-(phenylethynyl)phenyl]coumarin
7-Methoxy-3-trimethylsilylethynylcoumarin
7-Methoxy-3-[4-(trimethylsilylethynyl)phenyl]coumarin
7-Methoxy-3-[4-(phenylethynyl)phenyl]coumarin
3-[4-(Trimethylsilylethynyl)phenyl]benzo[5,6]coumarin
3-[4-(Phenylethynyl)phenyl]benzo[5,6]coumarin
7-(3-Methylpyrazole)-3-[4-(trimethylsilylethynyl)phenyl]coumarin
7-(3-Methylpyrazole)-3-[4-(phenylethynyl)phenyl]coumarin
7-(3,4-Dimethyltriazole)-3-[4-(trimethylsilylethynyl)phenyl]coumarin
7-(3-Dimethyltriazole)-3-[4-(trimethylsilylethynyl)phenyl]coumarin
7-(3-Phenyltriazole)-3-[4-(trimethylsilylethynyl)phenyl]coumarin
7-(Naphtho[1,2]triazol-2-yl)-trimethylsilylethynylcoumarin
7-(Naphtho[1,2]triazol-2-yl)-3-phenylethynylcoumarin These compounds may be used alone or in appropriate combinations of two or more.

The compounds of the invention may be produced by the known processes described below.

The pyrazoline compound represented by formula (I) may be obtained, for example, by condensing a ketone represented by formula (XIII):

[Chemical Formula 16]

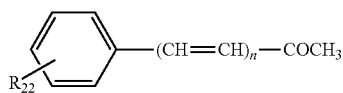

(wherein $R_{22}$ represents iodine or bromine, and n represents 0 or 1)
and a formyl compound represented by formula (XIV):

[Chemical Formula 17]

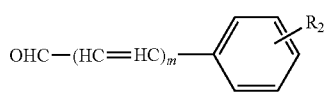

(wherein $R_2$ and m have the same definitions as above) in an ethanol aqueous solution in the presence of a basic catalyst such as piperidine, to produce an α,β-unsaturated carbonyl compound represented by formula (XV):

[Chemical Formula 18]

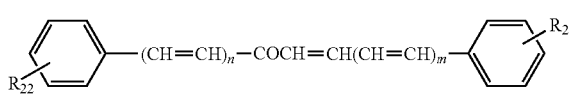

(wherein $R_2$, $R_{22}$, m and n have the same definitions as above).

Next, the α,β-unsaturated carbonyl compound represented by formula (XV) may be reacted with a phenylhydrazine represented by formula (XVI):

[Chemical Formula 19]

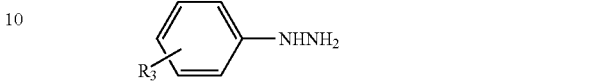

(wherein $R_3$ has the same definition as above) in acetic acid, and then reacted with trimethylsilylacetylene in THF and triethylamine, using bis(triphenylphosphine)palladium(II) dichloroide or tetrakis(triphenylphosphine)palladium(0) and copper iodide as the catalyst, to produce a pyrazoline compound represented by formula (I), which is substituted with a trimethylsilylethynyl group.

Instead of trimethylsilylacetylene there may be used phenylacetylene represented by formula (XVII):

[Chemical Formula 20]

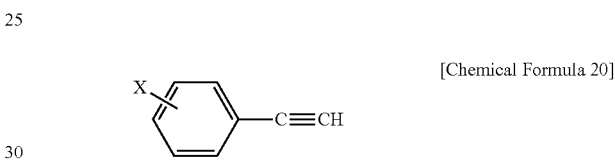

(wherein X has the same definition as above), to obtain a pyrazoline compound represented by formula (I):

[Chemical Formula 21]

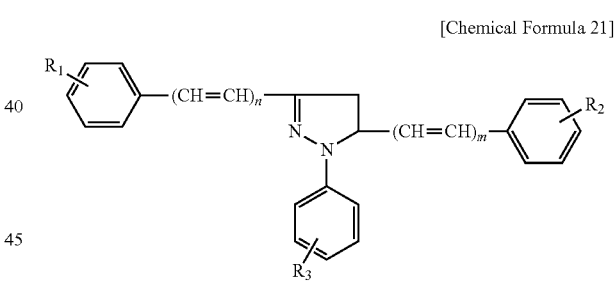

(wherein $R_1$, $R_2$, $R_3$, m and n have the same definitions as above),
which is substituted with a phenylethynyl group.

The coumarin compound represented by formula (III) can be obtained, for example, by condensing an aldehyde compound represented by formula (XVIII):

[Chemical Formula 22]

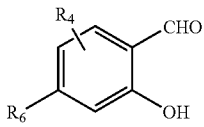

(wherein $R_4$ and $R_6$ have the same definitions as above) with a compound represented by formula (XIX):

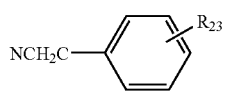

[Chemical Formula 23]

(wherein $R_{23}$ represents iodine or bromine) in an ethanol aqueous solution, in the presence of a basic catalyst such as piperidine, and then reacting it with trimethylsilylacetylene in THF and triethylamine, using bis(triphenylphosphine)palladium(II) dichloroide or tetrakis(triphenylphosphine)palladium(0) and copper iodide as the catalyst, to produce a compound represented by formula (III), which is substituted with a trimethylsilylethynyl group.

By using an appropriate phenylacetylene instead of trimethylsilylacetylene, it is possible to produce a coumarin compound represented by formula (III) which is substituted with a phenylethynyl group.

The coumarin compound represented by formula (XI) can be obtained, for example, by condensing a compound represented by formula (XX):

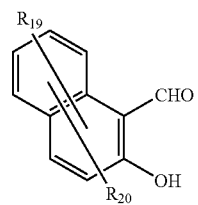

[Chemical Formula 24]

(wherein $R_{19}$ and $R_{20}$ have the same definitions as above) with a compound represented by formula (XXI):

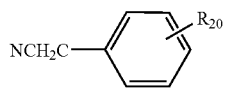

[Chemical Formula 25]

(wherein $R_{20}$ represents iodine or bromine)
in an ethanol aqueous solution, in the presence of a basic catalyst such as piperidine, and then reacting it with trimethylsilylacetylene in THF and triethylamine, using bis(triphenylphosphine)palladium(II) dichloroide or tetrakis(triphenylphosphine)palladium(0) and copper iodide as the catalyst, to produce a coumarin compound represented by formula (XI), which is substituted with a trimethylsilylethynyl group.

By using an appropriate phenylacetylene instead of trimethylsilylacetylene, it is possible to produce a coumarin compound represented by formula (XI) which is substituted with a phenylethynyl group.

The pyrazoline compounds and coumarin compounds of the invention have excellent ultraviolet absorptivity (molecular absorption coefficients) and quantum yield, and can therefore be effectively used as fluorescent agents in photosensitive resin fields and especially photoresist-related fields, in which increasingly higher speeds are employed, as well as in ultraviolet absorption films that cut harmful ultraviolet rays from sunlight and ultraviolet rays generated from illumination devices such as fluorescent lamps that attract flying insects, and as additives for ultraviolet absorption films that cut ultraviolet rays from sunlight and fluorescent lamps to prevent discoloration of photographs and liquid crystal displays.

The present invention will now be explained in greater detail by examples, reference examples and comparative examples, with the understanding that the invention is in no way limited only to the examples. The "parts" referred to in the examples all mean "parts by weight".

EXAMPLES

Example 1

After charging 4.6 parts of 1-phenyl-3,5-di(4-bromophenyl)pyrazoline synthesized by a known method, 2.4 parts of trimethylsilylacetylene, 0.46 parts of tetrakis(triphenylphosphine)palladium(0), 0.038 parts of copper iodide and 20 ml of triethylamine in 40 ml of THF, the mixture was stirred at 66° C. for 8 hours and then the reaction mixture was filtered and washed with THF. The obtained filtrate was concentrated, and the precipitate was filtered, washed, recrystallized from methanol and dried at 60° C. to obtain 4.4 parts of 1-phenyl-3,5-di(4-trimethylsilylethynylphenyl)pyrazoline having a melting point of 108-110° C.

Example 2

After charging 9.6 parts of 1-phenyl-3-(4-iodophenyl)-5-(4-t-butylphenyl)pyrazoline synthesized by a known method, 2.4 parts of trimethylsilylacetylene, 0.28 parts of bis(triphenylphosphine)palladium(II) dichloride, 0.04 parts of copper iodide and 40 mL of triethylamine in 80 mL of THF, the mixture was stirred at 60° C. for 10 hours. The reaction mixture was filtered, the obtained filtrate was concentrated, and the precipitate was filtered, washed, recrystallized from methanol and dried at 60° C. to obtain 5.6 parts of 1-phenyl-3-(4-trimethylsilylethynylphenyl)-5-(4-t-butylphenyl)pyrazoline having a melting point of 160-162° C.

Example 3

Reaction was conducted in the same manner with 2.4 parts of phenylacetylene instead of the trimethylsilylacetylene used in Example 1, to obtain 3 parts of 1-phenyl-3,5-di-(4-phenylethynylphenyl)pyrazoline having a melting point of 200-204° C.

Example 4

Reaction was conducted in the same manner with 2.4 parts of phenylacetylene instead of the trimethylsilylacetylene used in Example 2, to obtain 4.8 parts of 1-phenyl-3-(4-phenylethynylphenyl)-5-(4-t-butylphenyl)pyrazoline having a melting point of 190-192° C.

Example 5

After charging 12.0 parts of 1-phenyl-3 (4-bromostyryl)-5-(4-bromophenyl)pyrazoline synthesized by a known method, 6.0 parts of phenylacetylene, 0.46 parts of tetrakis(triphenylphosphine)palladium(0), 0.1 parts of copper iodide and 50 mL of triethylamine in 150 mL of THF, the mixture was stirred at 64° C. for 8 hours. The reaction mixture was filtered, the obtained filtrate was concentrated, and the precipitate was filtered, washed, recrystallized from ethanol and dried at 60° C. to obtain 5 parts of 1-phenyl-3-(4-phenylethynylstyryl)-5-(4-phenylethynylphenyl)pyrazoline having a melting point of 212-214° C.

Example 6

Reaction was conducted in the same manner with 6.0 parts of trimethylsilylacetylene instead of the phenylacetylene used in Example 5, to obtain 5 parts of 1-phenyl-3-(4-trimethylsilylethynylstyryl)-5-(4-trimethylsilylethynylphenyl)pyrazoline having a melting point of 128-130° C.

Comparative Example 1

After dissolving 2.5 parts of caustic soda in 15 parts of water, 43 parts of methanol was added and the mixture was stirred. To this was added a mixture of 8.1 parts of 4-tert-butylbenzaldehyde and 6 parts of acetophenone, and the obtained mixture was stirred at 20-30° C. for 4 hours. The obtained precipitate was filtered, 4.7 parts of phenylhydrazine was added, and the mixture was stored at 110° C. for 3 hours in 120 parts of glacial acetic acid. After cooling to room temperature, the precipitate was filtered, washed with methanol and dried at 60° C. to obtain 11.5 parts of 1-phenyl-3-phenyl-5-(4-tert-butylphenyl)pyrazoline having a melting point of 150-153° C.

Comparative Example 2

After dissolving 10 parts of caustic soda in 20 parts of water, 100 parts of methanol was added and the mixture was stirred. To this was added a mixture of 16.2 parts of 4-tert-butylbenzaldehyde and 2.8 parts of acetone, and the obtained mixture was stirred at 20-30° C. for 4 hours. The obtained precipitate was filtered, 4.7 parts of phenylhydrazine was added, and the mixture was stored at 110° C. for 4 hours in 120 parts of glacial acetic acid. After cooling, the precipitate was filtered, washed with methanol and dried at 60° C. to obtain 12.5 parts of 1-phenyl-3-(4-t-butylstyryl)-5-(4-t-butylphenyl)pyrazoline having a melting point of 188-192° C.

Reference Example A

Table 1 shows the results of measuring the maximum absorption wavelength (λmax) and molecular absorption coefficient using a UV-2400PC by Shimadzu Corp., and the results of measuring the quantum yield using an RF-5300PC by Shimadzu Corp., for each pyrazoline compound (or pyrazoline-based fluorescent agent) of the invention obtained in Examples 1-5, and each pyrazoline compound with no ethynyl group obtained in Comparative Examples 1-2.

Absorption measurement method: Each sample was dissolved in DMF to a 10 ppm concentration.

Quantum yield measurement method: Measurement of a preparation of each sample in ethanol, with an absorbance of 0.02 at an absorption wavelength of 366 nm (measurement with UV-2400PC by Shimadzu Corp.) (Quantum yield of sample calculated with quantum yield of standard anthracene as 0.3).

TABLE 1

| Sample compound | Maximum absorption wavelength λ max (nm) | Molecular absorption coefficient ε | Excitation wavelength λ ex (nm) | Fluorescent wavelength λ em (nm) | Quantum yield |
|---|---|---|---|---|---|
| Comp. Ex. 1 | 362 | 19588 | 360 | 453 | 0.42 |
| Example 1 | 391 | 25766 | 386 | 483 | 0.50 |
| Example 2 | 392 | 28447 | 386 | 485 | 0.50 |
| Example 3 | 395 | 36150 | 407 | 488 | 0.57 |
| Example 4 | 398 | 34095 | 412 | 489 | 0.55 |
| Comp. Ex. 2 | 387 | 34967 | 386 | 476 | 0.41 |
| Example 5 | 414 | 45039 | 423 | 513 | 0.52 |

As seen by the results in Table 1, the pyrazoline-based fluorescent agents of the invention had a shift of maximum absorption wavelength from the ultraviolet range to the visible short wavelength end, while the molecular absorption coefficients were also increased, compared to the pyrazoline compounds with no ethynyl group, of the comparative examples.

Example 7

After charging 6.2 parts of 7-diethylamino-3-bromo-4-methylcoumarin obtained by bromination of 7-diethylamino-4-methylcoumarin (C.I. Fluorescent Brightner 52), 2.4 parts of trimethylsilylacetylene, 0.46 parts of tetrakis(triphenylphosphine)palladium(0), 0.038 parts of copper iodide and 20 ml of triethylamine in 40 ml of THF, the mixture was stirred at 65° C. for 8 hours and the reaction mixture was filtered and washed with THF. The obtained filtrate was concentrated to obtain 4.6 parts of 7-diethylamino-3-trimethylsilylethynyl-4-methylcoumarin as an oil.

Example 8

After charging 5.2 parts of 7-methoxy-3-bromocoumarin obtained by bromination of 7-methoxycoumarin, 2.4 parts of trimethylsilylacetylene, 0.46 parts of tetrakis(triphenylphosphine)palladium(0), 0.038 parts of copper iodide and 20 ml of triethylamine in 40 ml of THF, the mixture was stirred at 65° C. for 10 hours and the reaction mixture was filtered and washed with THF. The filtrate was concentrated, and the obtained cake was recrystallized from methanol and dried at 60° C. to obtain 2.2 parts of 7-methoxy-3-trimethylsilylethynylcoumarin having a melting point of 130-132° C.

Example 9

Reaction was conducted in the same manner with 2.4 parts of phenylacetylene instead of the trimethylsilylacetylene used in Example 7, to obtain 2 parts of 7-diethylamino-3-phenylethynyl-4-methylcoumarin having a melting point of 142-144° C.

Example 10

Reaction was conducted in the same manner with 2.4 parts of phenylacetylene instead of the trimethylsilylacetylene used in Example 8, to obtain 3 parts of 7-methoxy-3-phenylethynyl-3-methylcoumarin having a melting point of 136-138° C.

Example 11

After charging 7.4 parts of 7-diethylamino-4-[(p-bromphenyl)]coumarin synthesized by a known method, 2.4 parts of phenylacetylene, 0.46 parts of tetrakis(triphenylphosphine)palladium(0), 0.038 parts of copper iodide and 20 ml of triethylamine in 40 ml of THF, the mixture was refluxed for 9 hours. The reaction mixture was filtered and washed with THF, and the obtained filtrate was concentrated and then diluted with water and filtered. The obtained cake was recrystallized from methanol. Upon drying under reduced pressure there was obtained 2.2 parts of 7-diethylamino-4-[4-(phenylethynyl)phenyl]coumarin having a melting point of 136-138° C.

Example 12

After charging 6.6 parts of 7-methoxy-4-[4-(p-bromophenyl)]coumarin synthesized by a known method, 2.4 parts of phenylacetylene, 0.46 parts of tetrakis(triphenylphosphine)palladium(0), 0.038 parts of copper iodide and 20 ml of triethylamine in 40 ml of THF, the mixture was refluxed for 9 hours. The reaction mixture was filtered and washed with THF, and the obtained filtrate was concentrated and then diluted with water and filtered. The obtained cake was recrystallized from methanol. Upon drying under reduced pressure there was obtained 2.6 parts of 7-methoxy-4-[4-(phenylethynyl)phenyl]coumarin having a melting point of 178-180° C.

Example 13

After charging 7 parts of 3-(p-bromphenyl)-benzo[5,6]coumarin synthesized by a known method, 2.4 parts of trimethylsilylacetylene, 0.46 parts of tetrakis(triphenylphosphine)palladium(0), 0.038 parts of copper iodide and 20 ml of triethylamine in 40 ml of THF, the mixture was refluxed for 9 hours. The reaction mixture was filtered and washed with THF, and the obtained filtrate was concentrated and then diluted with water and filtered. The obtained cake was recrystallized from methanol. Upon drying under reduced pressure there was obtained 3.7 parts of 3-(p-trimethylsilylethynylphenyl)-benzo[5,6]coumarin having a melting point of 126-130° C.

Example 14

After charging 7.6 parts of 7-(3-methylpyrazole)-3-(4-bromophenyl)coumarin synthesized by a known method, 2.4 parts of phenylacetylene, 0.46 parts of tetrakis(triphenylphosphine)palladium(0), 0.038 parts of copper iodide and 20 ml of triethylamine in 40 ml of THF, the mixture was refluxed for 9 hours. The reaction mixture was filtered and washed with THF, and the obtained filtrate was concentrated and then diluted with water and filtered. The obtained cake was recrystallized from methanol. Upon drying under reduced pressure there was obtained 3.4 parts of 7-(3-methylpyrazole)-3-[4-(p-phenylethynyl)phenyl]coumarin having a melting point of 135-137° C.

Example 15

After charging 7.8 parts of 7-(naphtho[1,2]triazol-2-yl)-3-bromocoumarin synthesized by a known method, 2.4 parts of trimethylsilylacetylene, 0.46 parts of tetrakis(triphenylphosphine)palladium(0), 0.038 parts of copper iodide and 20 ml of triethylamine in 40 ml of THF, the mixture was refluxed for 9 hours. The reaction mixture was filtered and washed with THF, and the obtained filtrate was concentrated and then diluted with water and filtered. The obtained cake was recrystallized from methanol. Upon drying under reduced pressure there was obtained 4 parts of 7-(naphtho[1,2]triazol-2-yl)-3-trimethylsilylethynylcoumarin having a melting point of 250-252° C.

Reference Example B

Table 2 shows the results of measuring the maximum absorption wavelength (λmax) and molecular absorption coefficient using a UV-2400PC by Shimadzu Corp., and the results of measuring the quantum yield using an RF-5300PC by Shimadzu Corp., for each coumarin compound (or coumarin-based fluorescent agent) of the invention obtained in Examples 7-15, and each known coumarin compound and coumarin fluorescent agent with no ethynyl group.

Absorption measurement method: Each sample was dissolved in DMF to a 10 ppm concentration.
Quantum yield measurement method: Measurement of a preparation of each sample in ethanol, with an absorbance of 0.02 at an absorption wavelength of 366 nm (measurement with UV-2400PC by Shimadzu Corp.) (Quantum yield of sample calculated with quantum yield of standard anthracene as 0.3).

TABLE 2

| Sample compound | Maximum absorption wavelength $\lambda$ max (nm) | Molecular absorption coefficient $\epsilon$ | Excitation wavelength $\lambda$ ex (nm) | Fluorescent wavelength $\lambda$ em (nm) | Quantum yield |
|---|---|---|---|---|---|
| C.I. Fluorescent Brightner 52 | 372 | 23793 | 370 | 433 | 0.58 |
| Example 7 | 414 | 27686 | 420 | 463 | 0.67 |
| Example 8 | 418 | 43028 | 427 | 472 | 0.68 |
| Example 9 | 416 | 41657 | 423 | 491 | 0.61 |
| 7-Methoxycoumarin | 324 | 5366 | 325 | 380 | unmeasurable |
| Example 10 | 355 | 25320 | 357 | 421 | 0.71 |
| Example 11 | 363 | 30737 | 365 | 433 | 0.76 |
| Example 12 | 355 | 38674 | 357 | 444 | 0.70 |

TABLE 2-continued

| Sample compound | Maximum absorption wavelength λ max (nm) | Molecular absorption coefficient ε | Excitation wavelength λ ex (nm) | Fluorescent wavelength λ em (nm) | Quantum yield |
|---|---|---|---|---|---|
| 3-Phenyl-benzo[5,6]coumarin | 364 | 18635 | 363 | 425 | 0.48 |
| Example 13 | 394 | 24235 | 392 | 484 | 0.60 |
| 7-(3-Methyl pyrazole)-3-phenylcoumarin | 353 | 22633 | 352 | 446 | 0.50 |
| Example 14 | 382 | 32056 | 380 | 478 | 0.69 |
| 7-(Naphtho[1,2]triazol-2-yl)coumarin | 367 | 23056 | 365 | 462 | 0.52 |
| Example 15 | 398 | 33008 | 396 | 493 | 0.65 |

As seen by the results in Table 2, the coumarin-based fluorescent agents of the invention had a shift of maximum absorption wavelength from the ultraviolet range to the visible short wavelength end, while the molecular absorption coefficients were also increased, compared to the known coumarin compounds and coumarin fluorescent agents both with no ethynyl group.

INDUSTRIAL APPLICABILITY

The pyrazoline compounds and coumarin compounds of the invention are compounds with high absorptivity (molecular absorption coefficients) in the ultraviolet-visible short wavelength range, and can be used as fluorescent agents for a variety of uses.

The invention claimed is:

1. A pyrazoline compound represented by formula (I):

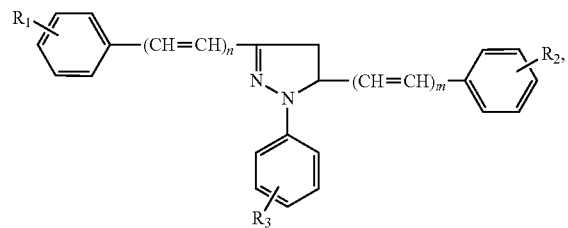

wherein $R_1$, $R_2$ and $R_3$ each independently represents hydrogen, halogen, $C_{1-8}$ alkyl, $C_{1-8}$ alkoxy, amino, an alkylamino or dialkylamino group having a $C_{1-8}$ alkyl group, sulfomethyl, sulfoamide, or a trimethylsilylethynyl group or a substituted or unsubstituted phenylethynyl group represented by formula (II):

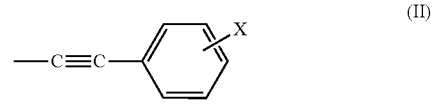

(wherein X represents hydrogen, halogen, $C_{1-3}$ alkyl or $C_{1-3}$ alkoxy), with the proviso that at least one of $R_1$, $R_2$ and $R_3$ represents a trimethylsilylethynyl group or phenylethynyl group; and m and n each represent 0 or 1.

2. A coumarin compound represented by formula (XI):

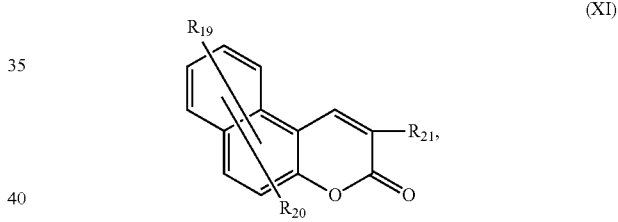

wherein $R_{19}$ and $R_{20}$ each independently represents hydrogen, $C_{1-4}$ alkyl, $C_{1-4}$ alkoxy or halogen; and $R_{21}$ represents a trimethylsilylethynyl group or a substituted or unsubstituted phenylethynyl group represented by formula (XII):

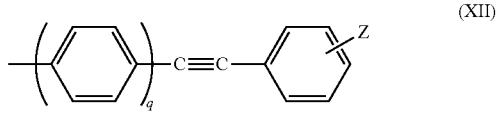

(wherein Z represents halogen, $C_{1-3}$ alkyl or $C_{1-3}$ alkoxy; and q represents an integer of 0-2).

* * * * *